US008325226B2

(12) United States Patent
Moriarty

(10) Patent No.: US 8,325,226 B2
(45) Date of Patent: Dec. 4, 2012

(54) DOCKABLE BACKLIGHT

(75) Inventor: Timothy Gerard Moriarty, Rochester, NY (US)

(73) Assignee: Quality Vision International, Inc., Rochester, NY (US)

( * ) Notice: Subject to any disclaimer, the term of this patent is extended or adjusted under 35 U.S.C. 154(b) by 278 days.

(21) Appl. No.: 12/829,619

(22) Filed: Jul. 2, 2010

(65) Prior Publication Data

US 2012/0002039 A1 Jan. 5, 2012

(51) Int. Cl.
*H04N 7/18* (2006.01)
(52) U.S. Cl. .................................. 348/131; 348/135
(58) Field of Classification Search .......... 348/125–133, 348/135–142
See application file for complete search history.

(56) References Cited

U.S. PATENT DOCUMENTS

| 4,629,319 | A | * | 12/1986 | Clarke et al. | 356/237.2 |
| 4,651,405 | A | | 3/1987 | McMurtry | |
| 6,057,924 | A | * | 5/2000 | Ross et al. | 356/632 |
| 6,161,940 | A | | 12/2000 | Choate et al. | |
| 7,266,420 | B2 | | 9/2007 | Budd | |
| 7,815,355 | B2 | * | 10/2010 | Thompson et al. | 362/560 |
| 2004/0075834 | A1 | | 4/2004 | Kaplan et al. | |
| 2004/0227948 | A1 | | 11/2004 | Debevec et al. | |

FOREIGN PATENT DOCUMENTS

JP 2008-151707 A 7/2008

OTHER PUBLICATIONS

PCT—Notification of Transmittal of the International Search Report and the Written Opinion of the International Searching Authority, or the Declaration; dated Feb. 9, 2012 in corresponding PCT International Application No. PCT/US2011/038868 (2 pages).
PCT—International Search Report dated Feb. 9, 2012 in corresponding PCT International Application No. PCT/US2011/038868 (3 pages).
PCT—Written Opinion of the International Searching Authority dated Feb. 9, 2012 in corresponding PCT International Application No. PCT/US2011/038868 (3 pages).

* cited by examiner

Primary Examiner — Andy Rao
(74) Attorney, Agent, or Firm — Stephen B. Salai, Esq.; Thomas B. Ryan; Harter Secrest & Emery LLP

(57) ABSTRACT

A machine vision system includes a table having a fixture for supporting an object under inspection above the table, a gantry supporting a camera further above the table, a docking station, and a profile light movable together with the gantry between an inspection position beneath the object and a docking position next to the docking station. Fittings are provided for releasably securing the profile light to the gantry and for releasably securing the profile light to the docking station. The profile light can be disengaged from the gantry and engaged with the docking station for moving the profile light to the docking position or disengaged from the docking station and reengaged with the gantry for moving the profile light to the inspection position.

14 Claims, 5 Drawing Sheets

DOCKABLE BACKLIGHT

BACKGROUND OF THE INVENTION

1. Field of the Invention

This application relates in general to machine vision systems and more particularly to a machine vision system with a detachable, dockable, backlight for enhancing the versatility of the inspection process.

2. Description of Related Art

It is often useful in machine vision systems, especially systems for inspecting objects to provide a backlight for illuminating the object from behind relative to the camera or imager (as used herein, camera includes both). Backlights permit features of the object, especially peripheral features, to be observed more clearly than when the object is directly illuminated. Such lighting is sometimes called profile lighting.

An example of an inspection system using a backlight is shown in U.S. Pat. No. 7,266,420. It is also useful in some applications to couple the backlight to the inspection camera so that the light and the camera move together when inspecting an object larger than the camera can image from a fixed location. The '420 patent accomplishes this by providing a large backlight and moving the camera. It is often desirable to provide a smaller backlight and move it with the camera. In cases where the object is supported between the backlight and the camera or in cases where the object is supported on a transparent deck with the light below the deck and the camera above it, this works well. However, there is a need for a machine vision system for inspecting objects that provides the option of direct illumination, back illumination, or both without the need for a transparent deck.

There is also a need for retrofitting existing coordinate measuring machines so that they can provide the function of video inspection systems. Coordinate measurement machines may have sensors such as contact probes that are movable in three dimensions to make measurements on an object under test. Such machines are frequently provided with massive tables for supporting the objects under test, often large granite tables. It is difficult to provide a profile light; that is, a light that illuminates the object-under-test from below, on such coordinate measuring machines. It has been contemplated to provide a complete transparent secondary or observation platform to support the article under test above the table and allow a profile light to move around underneath the article under test. Such platforms not only significantly increase the cost of upgrading the coordinate measuring machine to video inspection systems, but they compromise the load carrying capacity of the system.

There is a need for a method and apparatus for providing profile lighting in existing coordinate measuring machines that overcome these problems.

BRIEF SUMMARY OF THE INVENTION

It is an object of this invention to provide a video inspection system that is versatile enough to perform inspections with direct light and/or with backlight under machine control without the need for an operator to physically attach and remove the backlight.

It is an another object of this invention to provide a dockable profile light that can be detached from the moving structure of a video inspection system and placed in a dock, and then re-attached to the structure or optical system and automatically aligned and spatially synched with the camera without the need for recalibration.

It is another object of this invention to provide an apparatus for inspecting an object having a gantry movable between an inspection position and a docking position, and selectively configured to capture a profile light from a dock at the docking position and move the profile light and the camera to an inspection position with respect to an object being inspected.

Briefly stated and in accordance with a presently preferred embodiment of the invention, an apparatus for inspecting an object includes a table for supporting an object either on the surface of the table or supported above the surface, a gantry having spaced apart support legs and a horizontal beam extending between the support legs, a camera on the horizontal beam supported above the surface of the table by the gantry, fittings on the spaced apart support legs of the gantry for engaging a profile light, a profile light having fittings mating with the fittings on the spaced apart support legs, and a dock supported on the surface of the table for receiving and holding the profile light when not in use, the dock and the mating fittings arranged so that the gantry can be moved in position relative to the dock so that the profile light can be selectively removed from the dock for use or placed back in the dock when not being used. For inspecting using direct illumination, the object can be placed directly on the table. For inspecting with back illumination, the object is preferably supported above the table, the light is supported below the object, and the camera is supported above it.

BRIEF DESCRIPTION OF THE SEVERAL VIEWS OF THE DRAWING

While the novel aspects of the invention are set forth with particularity in the appended claims, the invention itself, together with further objects and advantages thereof may be more readily appreciated by reference to the following detailed description of several presently preferred embodiments in the invention taken in conjunction with the accompanying drawings.

DETAILED DESCRIPTION OF THE INVENTION

Figure 1:
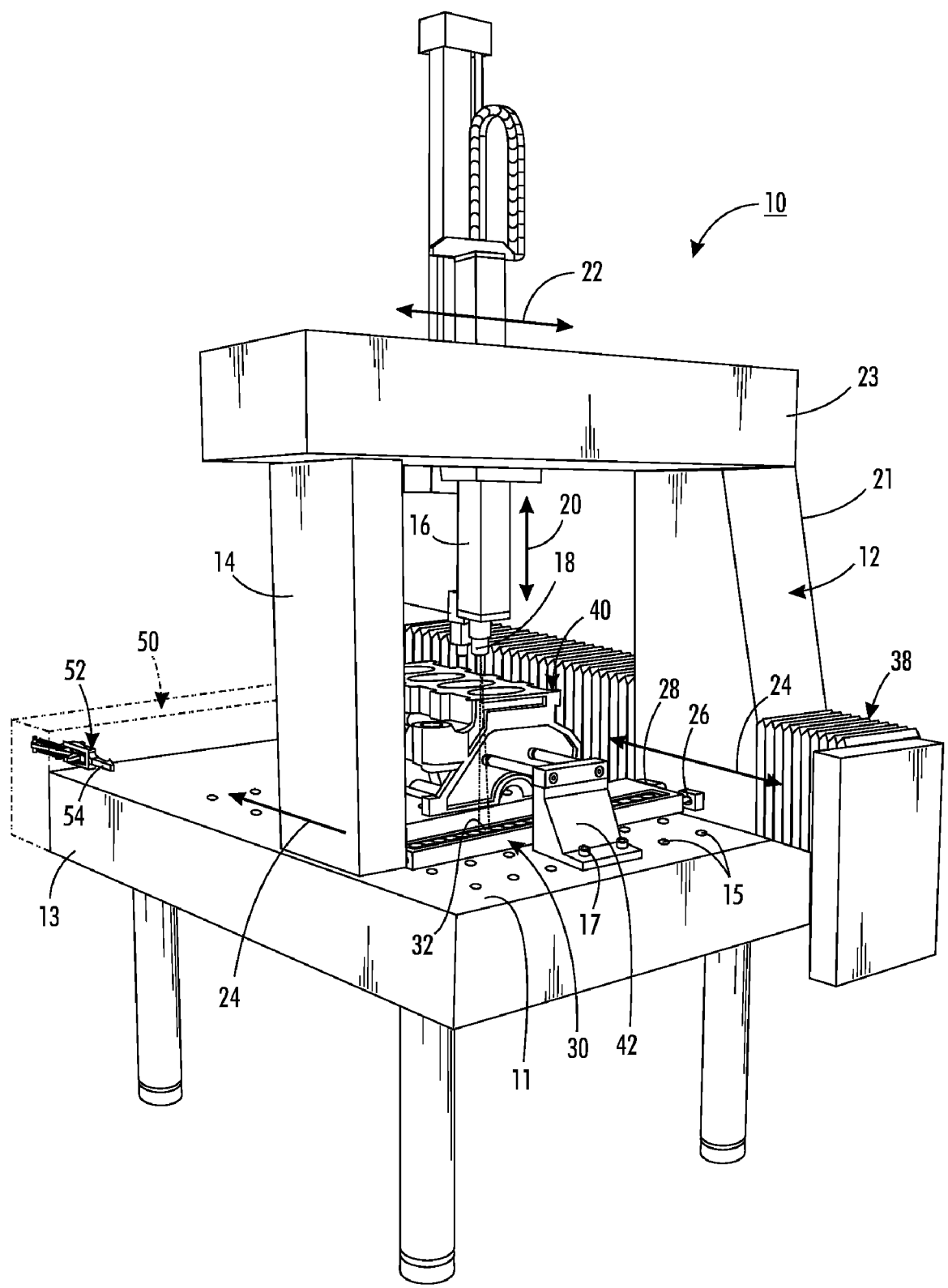
FIG. 1 is a perspective view of a machine vision system in accordance with this invention, showing a profile light supported on a gantry for illuminating the underside of a test object.

Referring now to FIGS. 1-5, a machine vision system in accordance with this invention is illustrated. FIG. 1 shows the machine vision system with a profile light in position and carried by a gantry also supporting a camera; the system is supported on a table that does not need to be transparent but could be.

The machine vision system 10 shown in FIG. 1 includes a substantially rigid table 13 having a preferably flat upper surface 11. Such tables may be made of granite or other similar materials such as steel that are rigid and capable of providing a mounting surface. The table 13 does not need to be transparent or translucent, but could be.

As shown in FIG. 1, a fixture 42 for supporting an object 40 under inspection in a position spaced above the top surface 11 of the table 13 is fastened to the table with fasteners such as bolts 17 or the like extending through the fixture 42 into the table 13. Mounting holes 15 are formed in the table for receiving the bolts 17 and securing the fixture 42 to the table 13. A gantry 12 is arranged to move back and forth in the directions indicated by the arrows 24 towards and away from the fixture 42 holding the object 40 under inspection. The gantry 12 includes two spaced apart support legs 14 and 21 and a horizontal beam 23 disposed on the upper ends of the support legs 14 and 21. Rails or ways (not shown) for guiding the gantry 12 may also be provided on the surface 11 of the table 13 or alongside the surface 11. A servo-drive-controlled linear actuator 38 moves the gantry 12 over the table 13. A camera 18, such as a video camera or other imaging device, is attached to a vertically movable arm 16, which moves as indicated by arrows 20 and is carried by the horizontal beam 23. The camera 18 is also translatable along the beam in the directions indicated by the arrows 22.

A profile light 30 is supported slightly above the surface 11 of the table 13 between the surface 11 and the object 40 under inspection by the opposed legs 14 and 21 of the gantry 12. As shown, fittings on of the gantry 12 include alignment fittings 26 having a V-shaped notches for receiving front pins 34 of the profile light 30 for accurately positioning the profile light 30 with respect to the gantry 12 and over-center latch fittings 28 for engaging rear pins 36 of the profile light 30 and securing both the front and rear pins 34 and 36 of the profile light 30 to the gantry 12. Similar front and rear pins 34 and 36 are provided at opposite ends of the profile light 30 for engaging similar alignment and latch fittings 26 and 28 on the inside surfaces of the two legs 14 and 21 of the gantry 12. The profile light 30 can have a generally rectangular configuration with the front and rear pins 34 and 36 extending from each of two opposite ends of the profile light 30 for engaging the fittings 26 and 28 on the legs 14 and 21 of the gantry 12. The pins 34 and 36 are preferably steel or another material that permits accurate alignment and accurate and repeatable positioning of the profile light 30 relative to the gantry 12, particularly relative to the camera 18, as the profile light 30 is repeatedly detached from and attached to the gantry 12.

Figure 2:
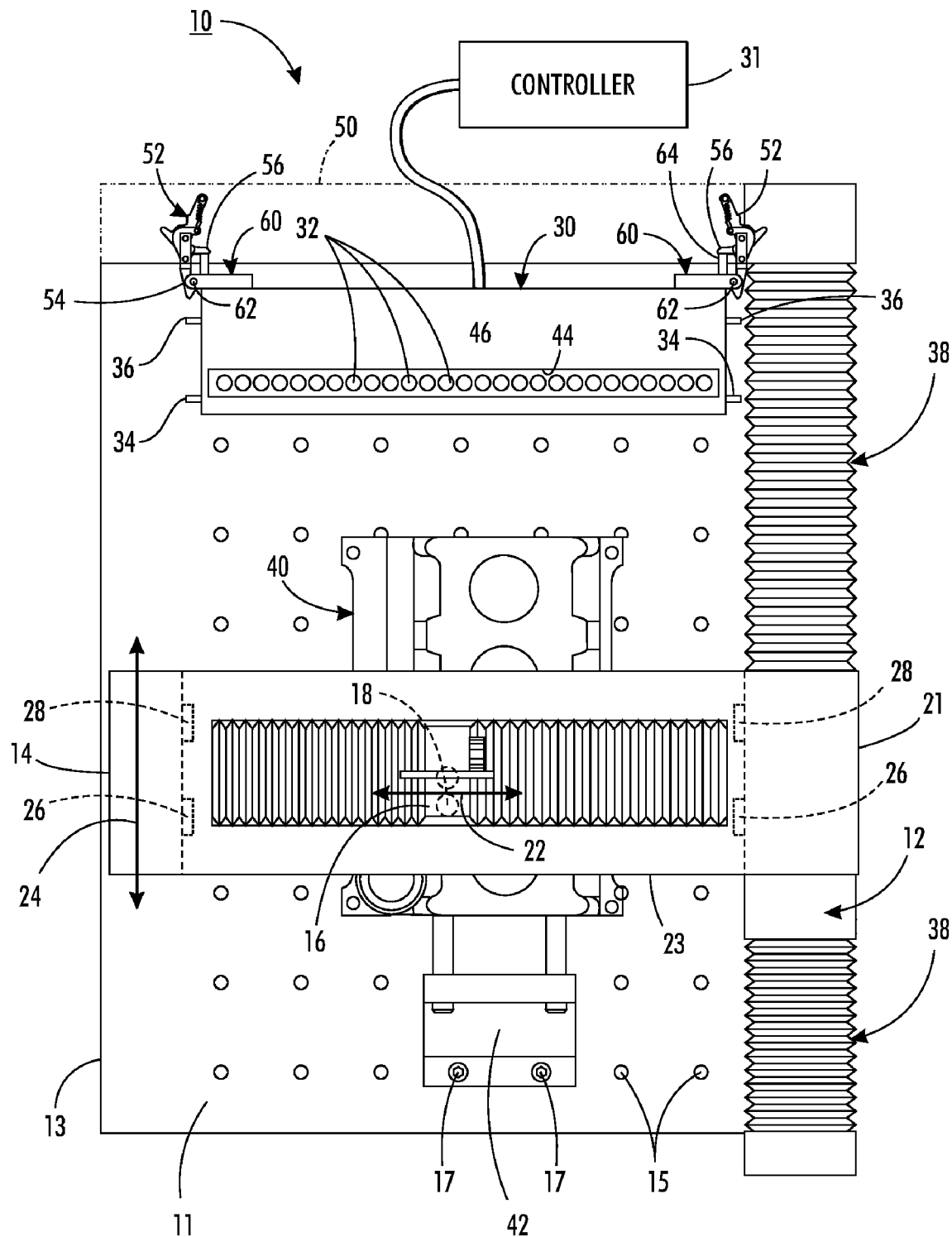
FIG. 2 is a top plan view thereof showing the profile light docked at a docking station.
Figure 3:
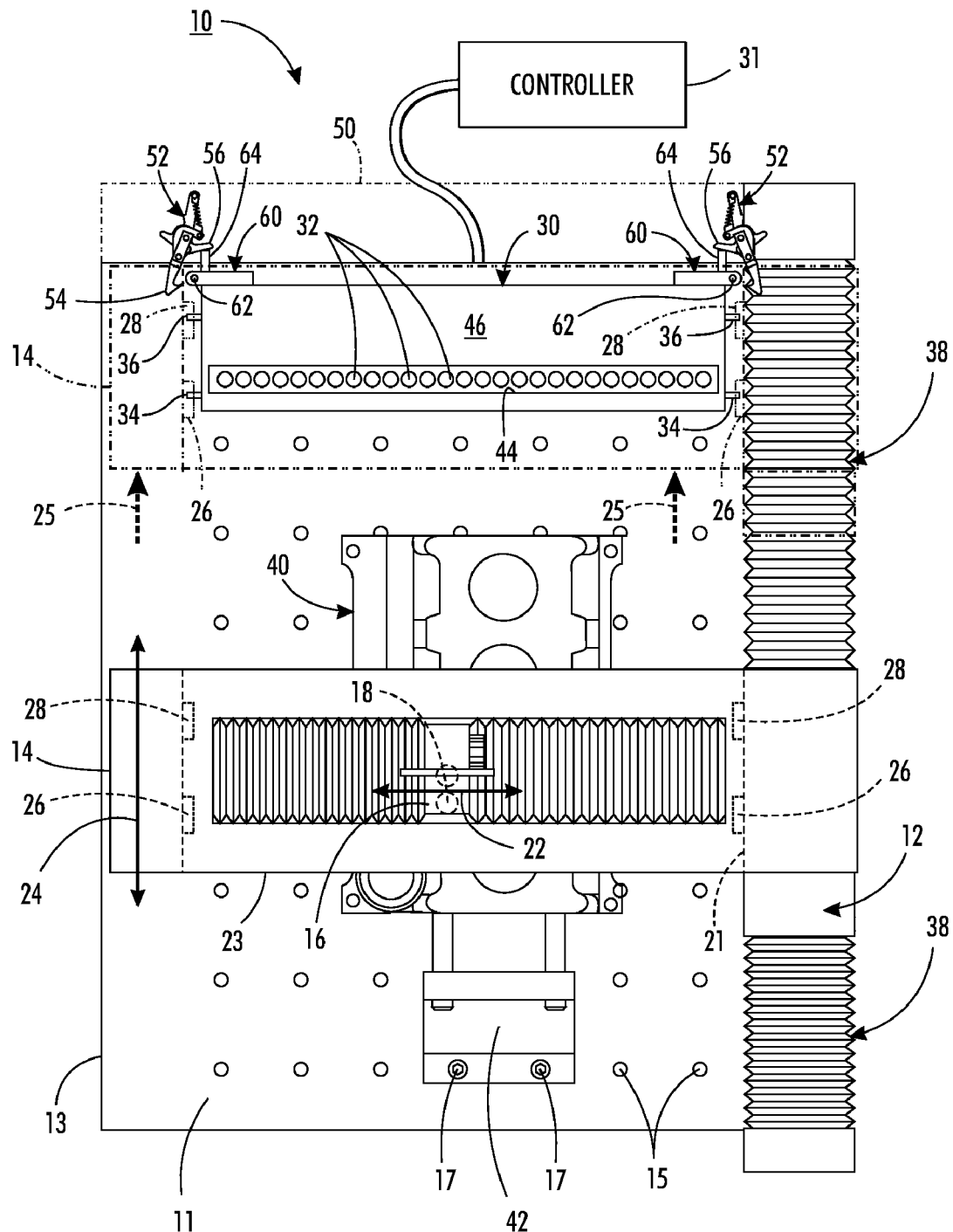
FIG. 3 is a top plan view thereof showing, in phantom, the gantry repositioned for docking or undocking the profile light from the docking station.
Figure 4:
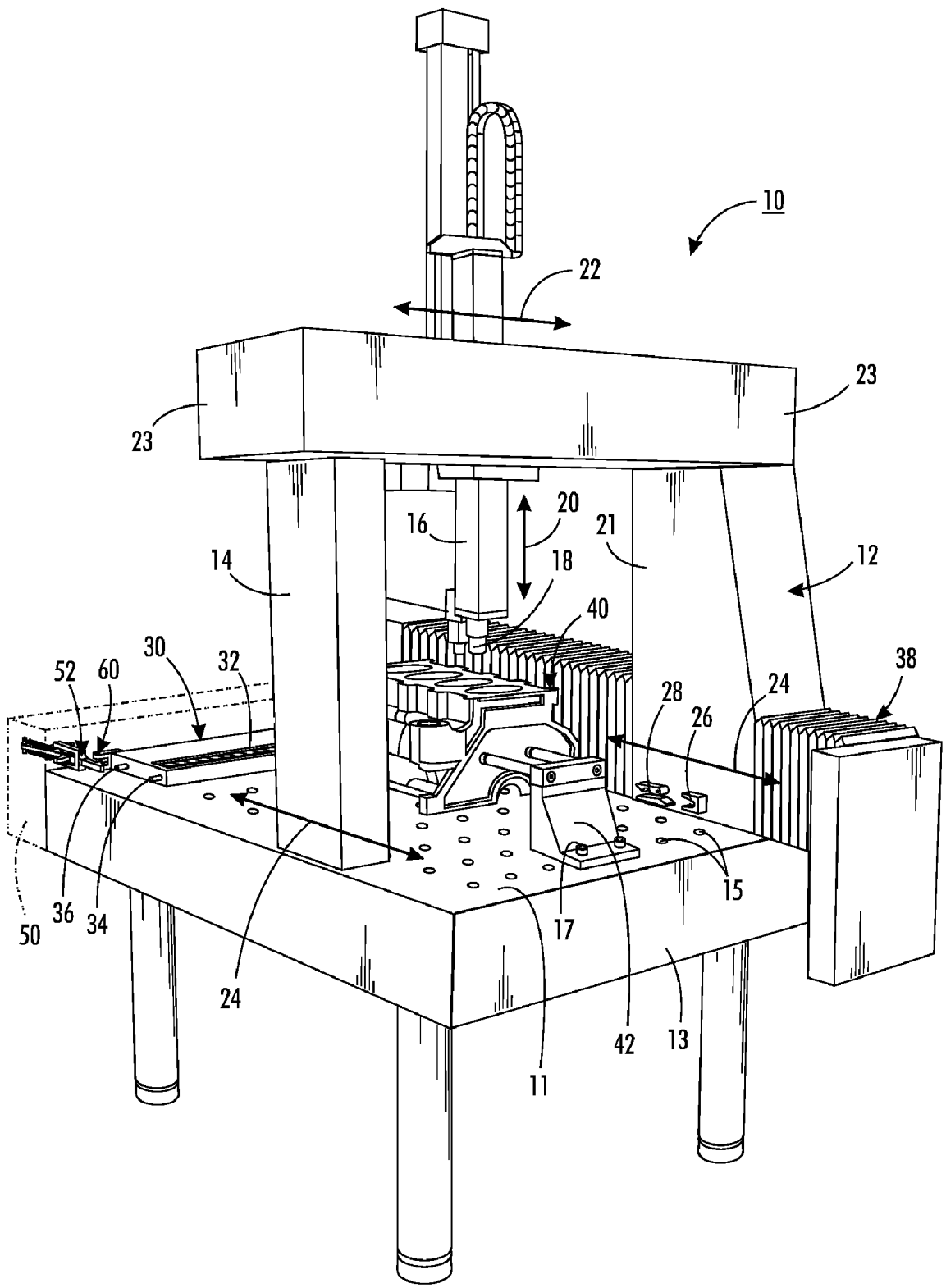
FIG. 4 shows the machine vision system of FIG. 1 with the profile light at the docking station.

An umbilical cord (not shown), such as an E-Chain® from igus Inc. of East Providence, R.I., provides electrical connection between a controller 31, which preferably includes a power supply, and the profile light 30. As shown in FIGS. 2 and 3, the profile light 30 is arranged with an output slot 44 on an upper surface of a box frame 46 through which light from a linear array (i.e., row) of controllable LED's 32 projects for illuminating the object 40 from below.

FIGS. 2-5 show the profile light 30 docked in a docking station 50 on the surface 11 of the table 13 at a position removed from the object 40 under inspection. Preferably, the docking station 50 (hereinafter referred to simply as a dock) includes as fittings latch mechanisms 52 (see particularly FIG. 5) and the profile light 30 includes as mating fittings striker assemblies 60 attached to the rear side of the profile light 30. The latch mechanisms 52, which project from the front of the dock 50, include spring-biased over-center latches 54 for engaging catch pins 62 of the striker assemblies 60 and toggles 56 for alternately retracting or resetting the over-center latches 54. When engaged with the catch pins 62 of the striker assemblies 60, the over-center latches 54 of the latch mechanisms 52 secure the profile light 30 to the dock 50.

The dock 50 is designed so that the gantry 12 can be moved as shown in phantom and by arrow 24 in FIG. 3 to position the profile light 30 at the dock 50. The gantry 12 can then be moved away from the dock 50, disengaging the fittings 26 and 28 on the gantry 12 from the pins 34 and 36 of the profile light 30 and leaving the profile light 30 at the dock 50 as shown in FIG. 2 for pick up later. The gantry 12 can then be used to move the camera 18 into position to inspect features of the object 40 or other objects not requiring a profile light or back illumination.

To park the profile light 30 at the dock 50, the gantry 12 is moved into position so that the catch pins 62 of the striker assemblies 60 carried by the profile light 30 engage the over-center latches 54 of the latch mechanisms 52 projecting from the dock 50. At the same position or nearly the same position, the latch fittings 26 and 28 of the gantry 12 are disengaged from the pins 34 and 36 at the ends of the profile light 30. The movement of the gantry 12 can then be reversed, leaving the profile light 30 behind secured to the dock 50.

To undock and reattach the profile light 30 to the gantry 12, the gantry 12 is moved into position for reengaging the latch fittings 26 and 28 of the gantry 12 with the pins 34 and 36 at the ends of the profile light 30. At the same or nearly the same position, the over-center latches 54 of the latch mechanisms 52 are disengaged from the catch pins 62 at the rear side of the profile light 30. The movement of the gantry 12 can then be reversed with the profile light 30 secured to the gantry 12.

For alternately engaging and disengaging with the various fittings of the profile light, the fittings of the gantry 12 or dock 50 can be arranged with toggles for alternately arming or disarming the latches. For example, the latch mechanisms 52 projecting from the dock 50 include toggles 56, and the striker assemblies 60 on the profile light 30 include reset posts 64. Contact between the toggles 56 and the reset posts 64 can be used to arm the latch mechanisms 52 for engaging the catch pins 62 of the striker assemblies 60 or to disarm the latch mechanisms 52 for disengaging the catch pins 62 of the striker assemblies 60. For example, the toggles 56 can be biased into an armed position but contact with the reset posts 64 can overcome the bias to disarm the latch mechanisms 52. When the reset posts 54 are moved out of contact, the toggles 56 return to their armed position at which the latch mechanisms 52 are capable of reengaging the catch pins 62.

Figure 5:
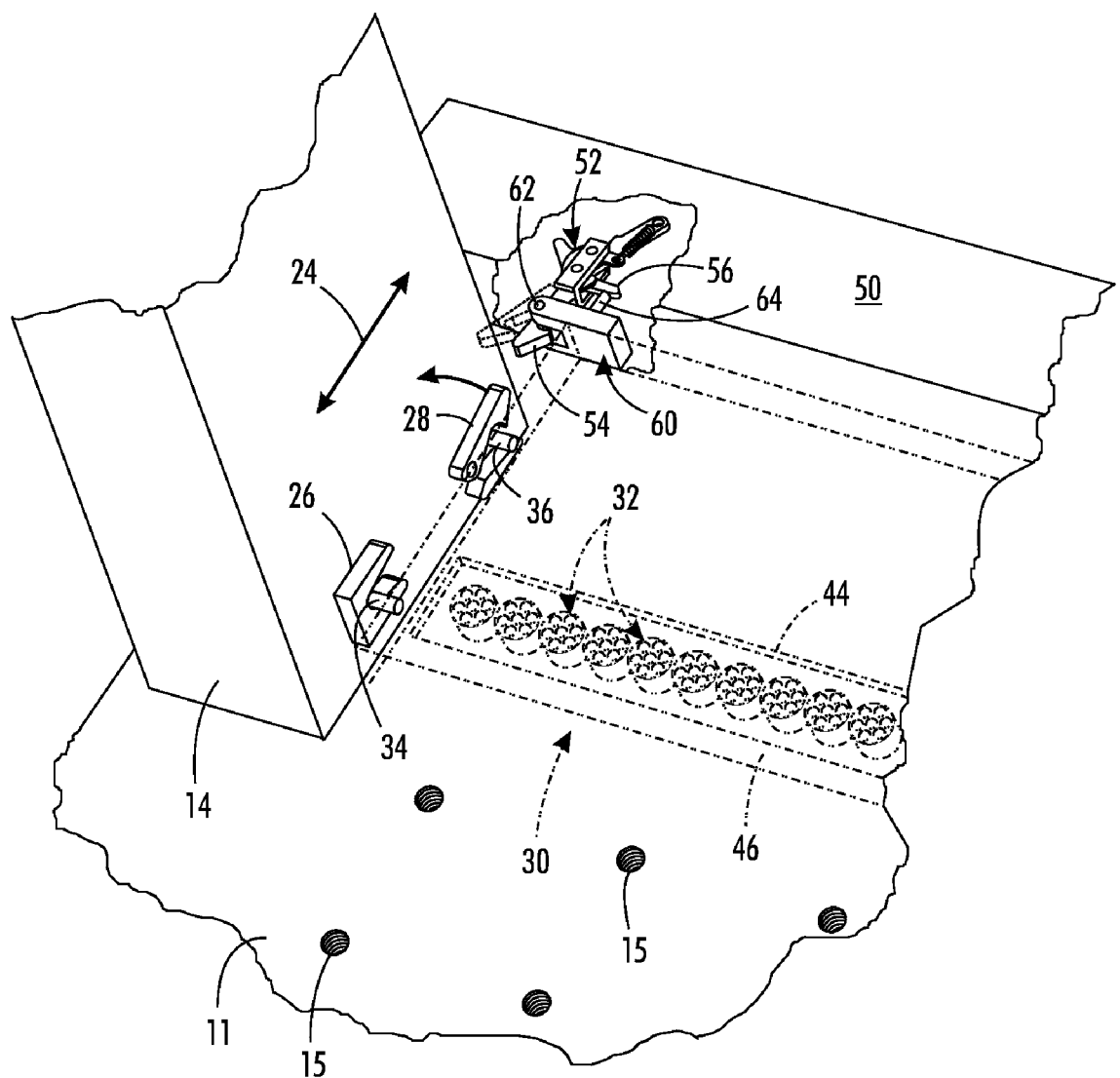
FIG. 5 is an enlarged fragmenting view of the profile light and fittings for alternately fastening the profile light to the gantry or the docking station.

As can be seen in FIG. 5, the gantry 12 can be moved into engagement with the docked profile light 30 by moving the notched fittings 26 of the gantry 12 into engagement with the front pins 34 of the profile light 30 and closing the over-center latch fittings 28 of the gantry 12 over the rear pins 36 of the profile light 30. The gantry 12 is then (this can be part of a single movement) moved slightly further toward the dock 50, as indicated in phantom by arrows 25 in FIG. 3, pushing reset posts 64 of the striker assemblies 60 against the toggles 56 of the latch mechanisms 52 for disarming and retracting the over-center latches 54 from the catch pins 62 of the striker assemblies 60 and thereby releasing the profile light 30 from the dock 50. The gantry 12 together with the reattached profile light 30 can than be moved into position, as shown in FIG. 1, for inspecting the object 40. The support pins 34 and 36 on the profile light 30 and the fittings 26 and 28 on the gantry cooperate to ensure that the profile light 30 is repeatedly and accurately aligned with the camera 18, which is also carried by the gantry 12.

Although the latch mechanisms 52 are shown projecting from the dock 50 and the striker assemblies 60 are shown attached to the profile light 30, the latch mechanisms 52 could be arranged to project from the profile light 30 and the striker assemblies could be attached to the dock 50 for achieving similar results. Similarly, either or both the support pins 34 and 36 at opposite ends of the profile light 30 could be reversed with the fittings 26 and 28 on the inside surfaces of the gantry legs 14 and 21.

A number of different types of fittings can be used for alternately securing the profile light 30 to either the gantry 12 or the dock 50, including mechanisms for detaching one set of fittings while the other set of fittings are attached. Trip switches, lever arms, and other mechanisms can be used for this latter purpose, including forming one of both sets of fittings with magnetic or electromagnetic latches that can be relatively powered for attaching or releasing the profile light 30.

For example, a set of levers can be used to arm or disarm latches on both the gantry 12 and the backlight 30 depending on set positions. To undock the profile light 30 according to this further example, the gantry 12 moves into the dock 50 with the gantry latch in the armed position. Upon reaching the dock 50, the gantry latch locks onto the profile light. At this same position, a lever opens to disarm the dock latch. Stopping immediately and retracting the gantry 12 will pull the profile light 30 out of the dock 50. To dock the profile light 30, the gantry 12 moves into the dock 50 slightly past the previous position (e.g. by one-quarter inch), and in this new position the gantry latch is armed (i.e., locks onto the profile light 30) and the gantry latch is disarmed (i.e., opened) allowing the profile light 30 to stay in the dock 50. As the gantry moves back out past the previous position the gantry latch is re-armed for engaging the profile light 30 on a next encounter.

Yet another example envisions the use magnets to hold the profile light 30 in the dock 50. The magnets would be strong enough to hold the profile light 30 in position in the dock 50 but the gantry latches would be stronger and overpower the magnets to extract the profile light 30. The magnets, which could be electromagnets, could be alternately powered or unpowered to alternately attach the profile light 30 to one or the other of the gantry 12 and the dock 50.

Preferably, the profile light 30 will always be connected to a controller 31 and power source, which can be intrinsic or extrinsic to the controller 31. An umbilical cord, which may be an E-Chain®, carries power and control signals to the light box as it moves through its full range of travel.

Preferably, the light emitting diodes 32 of the profile light 30, which are arranged in one or more rows, can be illuminated individually or in contiguous or non-contiguous groups. In addition to the alignment provided by the fittings 26, 28, and 34, 36 for locating the one or more rows of light emitting diodes 32 in alignment with (i.e., directly under) the entrance optics of the camera 18 in the direction of arrows 24, the light emitting diodes 32 are also preferably spatially synchronized with the camera 18, so that as the camera 18 is moved in the direction of arrows 22, only the light emitting diodes 32 directly under the entrance optics of the camera 18 are illuminated. This improves the profile image of the object 40 formed in the camera 18 by back illuminating the object 40 with a more collimated form of light.

While a single docking station 50 and a single profile light 30 have been illustrated in connection with a preferred embodiment of the invention, the invention also contemplates that multiple profile lights and/or multiple docking stations could be used. The docking stations and profile lights can be located at opposite ends of the travel of the gantry and/or may be disposed at different heights above the table.

While the invention has been described in connection with certain presently preferred embodiments thereof, those skilled in the art will recognize that many modifications and changes may be made therein without departing from the true spirit and scope of the invention, which is intended to be defined solely by the appended claims.

The invention claimed is:

1. Apparatus for inspecting an object comprising
   a table for supporting an object on a surface of the table or above the surface,
   a profile light for illuminating the object,
   a gantry supporting a camera and being slidably movable with respect to the surface of the table and including spaced apart support legs and a horizontal beam extending between the legs for supporting the camera above the object,
   fittings on the spaced apart support legs of the gantry for selectively releasably engaging the profile light;
   the profile light having mating fittings that are engageable with the fittings on the spaced apart support legs of the gantry for supporting the profile light beneath the object, and
   a dock on the table having fittings for releasably securing the profile light,
   the fittings of the dock and the fittings of the gantry being arranged so that the gantry can be moved to a position relative to the dock where the fittings of the dock engage the profile light so that the profile light may be selectively placed in and removed from the dock.

2. Apparatus for inspecting an object according to claim 1 comprising
   a fitting on the surface of the table for supporting the object above the surface of the table a sufficient distance for the profile light to move under the object while supported by the gantry.

3. Apparatus for inspecting an object according to claim 1 in which the profile light comprises a plurality of lights arranged in a row.

4. Apparatus for inspecting an object according to claim 1 in which the mating fittings on the profile light comprise pins projecting from an end of the profile light.

5. Apparatus for inspecting an object comprising
   a table for supporting an object on a surface of the table or above the surface,
   a gantry slidably movable with respect to the surface of the table and including spaced apart support legs and a horizontal beam extending between the legs supporting a camera above the surface,
   fittings on the spaced apart support legs of the gantry for selectively releasably engaging a profile light;
   a profile light having mating fittings, and
   a dock on the table for releasably securing the profile light,
   the dock and the fittings arranged so that the gantry can be moved in position relative to the dock where the fittings engage the profile light so that the profile light may be selectively placed in and removed from the dock,
   wherein the fittings on the gantry include alignment fittings for repeatably accurately positioning the profile light relative to the gantry.

6. Apparatus for inspecting an object according to claim 5 in which the fittings on the gantry include latch fittings for engaging pins on the profile light.

7. Apparatus for inspecting an object according to claim 1 in which the fittings on the support legs of the gantry comprise fittings that provide for repeatably positioning the profile light laterally and vertically with respect to the support legs.

8. A machine vision system comprising
   a table including a fixture for supporting an object under inspection,
   a gantry supporting a camera above the table being movable along the table, a docking station, a profile light movable together with the gantry between an inspection position at which the camera is located above the object and the profile light is located beneath the object and a docking position at which the profile light is located next to the docking station, a first set of fittings that releasably secure the profile light to the gantry, a second set of fittings that releasably secure the profile light to the docking station, and the first and second set of fittings allowing for the profile light (a) to be disengaged from the gantry and engaged with the docking station for moving the profile light to the docking position and (b) to be disengaged from the docking station and reengaged with the gantry for moving the profile light to the inspection position.

9. The machine vision system of claim 8 in which the gantry is movable independently of the profile light along the table when the profile light is in the docking position.

10. The machine vision system of claim 8 in which the first set of fittings includes an alignment fitting for accurately locating profile light with respect to the gantry and a latching fitting for releasably securing the profile light to the gantry.

11. The machine vision system of claim 10 in which the second set of fittings includes a latching mechanism for releasably securing the profile light to the docking station and the latching mechanism includes a toggle for alternately retracting and resetting the latching mechanism.

12. A method of operating a machine vision system comprising moving a gantry together with a camera along a table from a first position adjacent to a fixture for supporting a test object above the table to a second position adjacent to a docketing station, engaging fittings associated with a profile light with fittings associated with the gantry for securing the profile light to the gantry at the second position, disengaging other fittings associated with the profile light from fittings associated with the docketing station for releasing the profile light source from the docketing station, and moving the gantry together with the camera and the profile light from the second position adjacent to the docketing station to the first position adjacent to the fixture for illuminating the object under inspection with the profile light from beneath the object and imaging the object under inspection with the camera from above the object.

13. The method of claim 12 in which the step of engaging involves moving the gantry toward the docking station and the step of disengaging involves moving the gantry further toward the docking station.

14. The method of claim 12 including steps of moving the gantry together with the camera and the profile light from the first position adjacent to the fixture to the second position adjacent to the docketing station, disengaging the fittings associated with the profile light source from the fittings associated with the gantry for releasing the profile light source from the gantry at the second position, engaging the other fittings associated with the profile light source with the fittings associated with the docketing station for securing the profile light source to the docketing station, and moving the gantry independently of the profile light from the second position adjacent to the docketing station to the first position adjacent to the fixture for inspecting the object without illuminating the object from beneath using the profile light.

* * * * *